United States Patent
Jen et al.

(10) Patent No.: US 7,003,077 B2
(45) Date of Patent: Feb. 21, 2006

(54) METHOD AND APPARATUS FOR X-RAY ANODE WITH INCREASED COVERAGE

(75) Inventors: Sherman Chih-Yee Jen, Mequon, WI (US); Mark Ernest Vermilyea, Niskayuna, NY (US)

(73) Assignee: General Electric Company, Schnectady, NY (US)

( * ) Notice: Subject to any disclaimer, the term of this patent is extended or adjusted under 35 U.S.C. 154(b) by 98 days.

(21) Appl. No.: 10/605,508

(22) Filed: Oct. 3, 2003

(65) Prior Publication Data

US 2005/0074094 A1    Apr. 7, 2005

(51) Int. Cl.
*H01J 35/08*    (2006.01)
(52) U.S. Cl. ............................ 378/124; 378/4; 378/144

(58) Field of Classification Search ................ 378/124, 378/144, 4–20
See application file for complete search history.

(56) References Cited

U.S. PATENT DOCUMENTS

| | | | |
|---|---|---|---|
| 4,965,726 A | * 10/1990 | Heuscher et al. | ............. 378/19 |
| 5,485,493 A | 1/1996 | Heuscher et al. | |
| 5,625,661 A | 4/1997 | Oikawa | |
| 6,125,167 A | * 9/2000 | Morgan | ...................... 378/124 |
| 6,188,747 B1 | * 2/2001 | Geus et al. | .................. 378/124 |

\* cited by examiner

*Primary Examiner*—Craig E. Church
(74) *Attorney, Agent, or Firm*—Peter J. Vogel

(57) ABSTRACT

The present invention is an x-ray tube anode with two targets oriented back-to-back. The targets have separate and opposing cathodes. The targets are a fixed distance apart and rotate together on the same bearing shaft. The cathodes are mounted at either end of the vacuum tube. The cathodes may operate simultaneously or independent of each other based on the CT application.

22 Claims, 2 Drawing Sheets

METHOD AND APPARATUS FOR X-RAY ANODE WITH INCREASED COVERAGE

BACKGROUND OF INVENTION

The present invention relates generally to x-ray tubes and more particularly to x-ray tubes for volume computed tomography (CT) protocols.

A volume CT scan is typically generated by rotating an x-ray tube around an examination area while a subject is moved through the examination area. Cardiac screening, lung cancer evaluation and other volume CT protocols require larger coverage areas. Current technology requires lengthy scan times and requires elongated breath hold times from a subject in order to image an entire region of interest.

Several techniques have been applied in order to increase coverage of the x-ray anode, thereby reducing scan time and improving the subject's comfort level. For example, in one technique, x-rays are collimated from a single focal spot into two or more planes of radiation. However, the planes are not parallel and only a small number of planes are generated. Therefore, several revolutions are needed to cover any significant volume.

Another approach moves the x-ray tube in a circular path, with the focal spot of x-rays reciprocating at high speed. The focal spot of x-rays moves on a plane of ribbon. However, the focal spot is removed from the target, meaning it is spaced a distance from the target. Further, the focal spot is too big. The result of these two drawbacks is a fuzzy image. Yet another approach uses two targets and a single source to produce an x-ray fan beam having a width of 88 mm. While the width is larger than conventional beam widths, which are typically on the order of 60 mm, the quality of the image becomes compromised due to distortion of the image.

To avoid image distortion and obtain a high quality image, it is necessary to maintain the x-ray beam as flat as possible. In the approach that uses an 88 mm width, a true flat slice is not taken. The scan helix becomes flattened and upon reconstruction of the image using an x-ray that is not flat, the image appears distorted. Other approaches include a larger diameter anode and a plurality of x-ray tubes within a common gantry.

There is a need for an x-ray anode that provides a thick fan beam for improved coverage at the detector resulting in shorter scan times for volume CT applications without compromising the quality of the image.

SUMMARY OF INVENTION

The present invention is an x-ray tube anode with two targets oriented back-to-back. The targets have separate and opposing cathodes. The targets are a fixed distance apart and rotate together on the same bearing shaft. The cathodes are mounted at either end of the vacuum tube. The cathodes may run simultaneously or independently based on the CT application. When the cathodes are operated simultaneously, the x-ray coverage at the detector may be as high as 120 mm.

Objects and advantages of the present invention will become apparent upon reading the following detailed description and appended claims, and upon reference to the accompanying drawings.

BRIEF DESCRIPTION OF DRAWINGS

For a more complete understanding of this invention, reference should now be had to the embodiments illustrated in greater detail in the accompanying drawings and described below by way of examples of the invention. In the drawings:

FIG. 2 is a cross section of the x-ray tube in one embodiment of the present invention; and.

DETAILED DESCRIPTION

Figure 1:
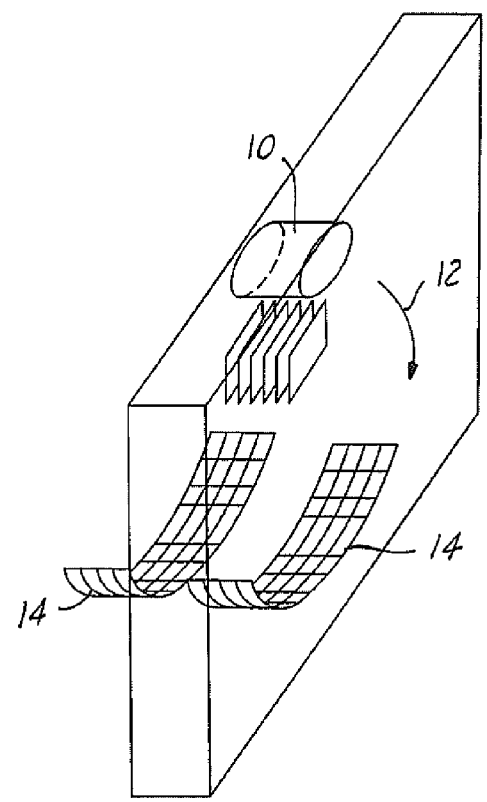
FIG. 1 is a block diagram of the anode of the present invention in a CT application.

Referring to FIG. 1, there is shown the x-ray tube 10 of the present invention on a rotating gantry 12, along with a detector 14 as it would be arranged for a volume CT application. While the embodiment shown is for a volume CT application and includes two grid detectors, it should be noted that it is for example purposes only and one skilled in the art is capable of using the x-ray tube 10 in another application or substituting detectors and the arrangement thereof in a CT application without departing from the scope of the present invention. A collimator 16 collimates the x-rays from the focal points into planes of radiation. The gantry 12 rotates about an axis moving the x-ray tube 10 and the detector 14 along with it.

Figure 2:
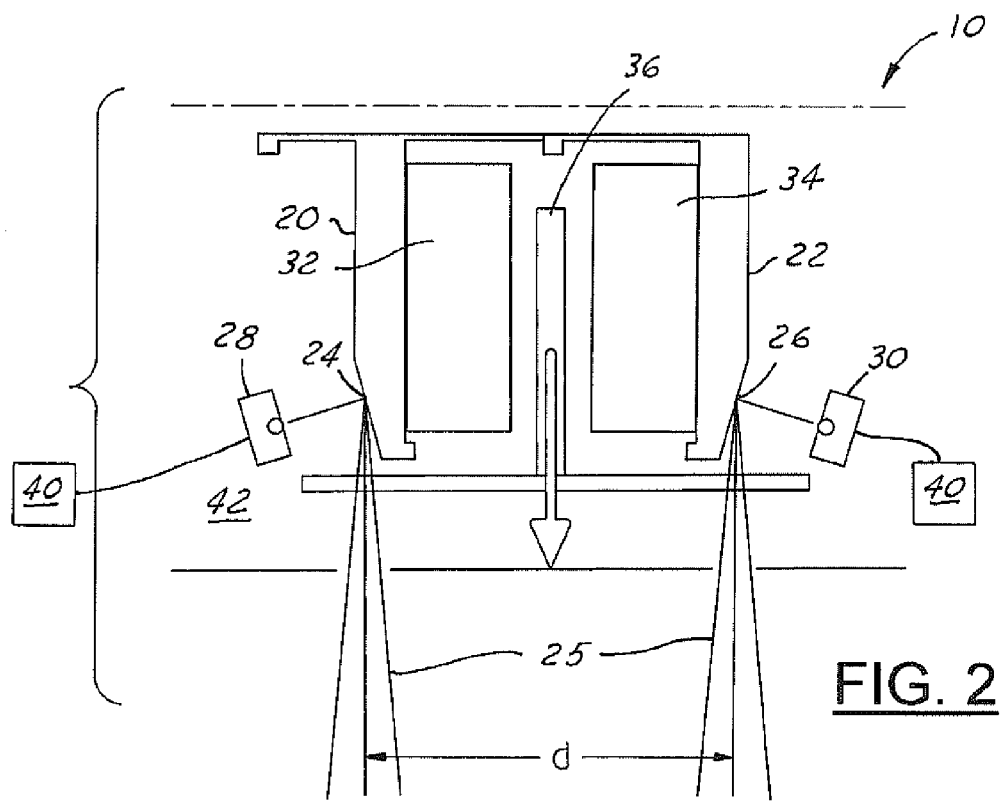

Referring to FIG. 2 a cross section of the x-ray tube 10 is shown. The x-ray tube is a vacuum tube and is typically surrounded by a shielded casing 18. Within the x-ray tube, there are two anodes 20, 22 each having a target 24, 26. The anodes 20, 22 are rotatably mounted. The targets 24, 26 are positioned on the front face of each anode. The targets 24, 26 are facing away from each other in a back-to-back arrangement. Cathodes 28 and 30 generate electron beams that are focused at the targets 24, 26. The heat generated at the anodes 20 and 22 is collected by storage members 32, 34 mounted to the back face of each anode 20, 22. The storage members 32, 24 are typically of a material that retains heat, such as graphite.

The back to back arrangement of the targets 24, 26 allows each anode 20, 22 to produce an x-ray beam 25 of substantial width and still be spaced far enough away from each other to double the coverage area and maintain high voltage stability. Further, the arrangement provides for separate and opposing cathodes to be used for each anode face, while maintaining a sufficient separation between the cathodes to avoid an over abundance of heat generated at the anode. The back-to-back arrangement of the targets 24 and 26 in conjunction with the individual cathodes 28, 30 for each anode maintains a flat x-ray beam and will provide a true double helical scan with a true image upon reconstruction of the scan.

Because the anode arrangement of the present invention creates double the heat, a heat sink 36 is positioned between the heat storage members 32, 34 mounted to the anodes 20, 22 for the purpose of heat dissipation. The heat sink 36 is typically copper or some other suitable heat conducting material. An oil 42, or other suitable substance, is provided in the housing 18 to dissipate the heat, shown by a block arrow, carried away by the heat sink 36. The heat is dissipated through the heat sink 36 and the oil 42. Excess heat has caused limitations in prior art designs.

The present invention is advantageous in that it provides double the coverage and still maintains high voltage stability. The distance between a cathode and any other part should be at least two inches to avoid arcing between components. If the distance between the cathode and a neighboring part is less than two inches, high voltage stability is compromised. The cathode arrangement in the present invention maintains the minimum distance to any other part of the x-ray tube.

The cathodes 28 and 30 of the present invention focus the electron beam and traject the electrons onto their respective target 24 and 26. The targets 24 and 26 direct the electron beams through the collimator, creating x-ray fan beams. Each beam is on the order of 60 mm in width. Therefore, together, the x-ray coverage at the detector could be as high as 120 mm without sacrificing the quality of the image upon reconstruction.

A high voltage controller 40 operates the cathodes 28 and 30. The cathodes may run independently, or simultaneously, based on the CT application. When the cathodes 28 and 30 are run simultaneously, the x-ray coverage at the detector is on the order of 120 mm. If run independent of one another, one cathode provides coverage similar to current machines.

A fixed distance, or pitch, d, is maintained between the targets 24 and 26. The pitch, d, is fixed and is not adjustable. As stated earlier, the distance remains fixed in order to maintain the proper distance to the cathode and to avoid arcing that compromises high voltage stability.

Figure 3:
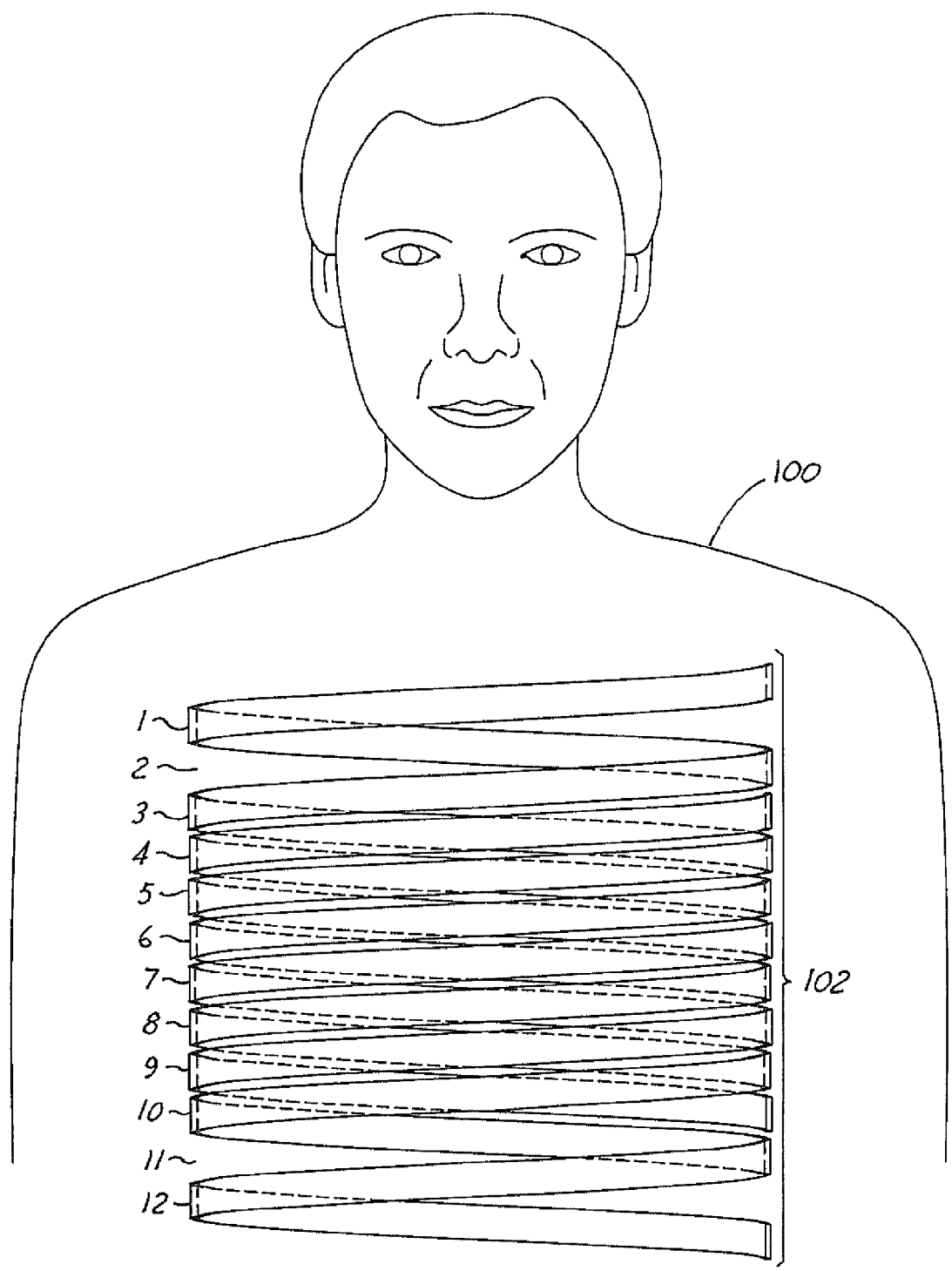
FIG. 3 is an example scan pattern for simultaneous operation of both cathodes according to the present invention.

During operation of both cathodes simultaneously, the coverage is as follows. Referring to FIG. 3, the invention will be described as it is used in a volume CT scanning application. A subject 100 is positioned in a CT machine, not shown, and an area to be imaged 102 is defined. The area shown in FIG. 3 is divided into twelve tracks, 1 through 12. There are 12 tracks shown for example purposes only and in no way should be interpreted as a limitation of the present invention.

The targets, Target 1 and Target 2, rotate about the subject as described above and create the scan pattern shown in FIG. 3. Due to the fixed spacing of the targets, Target 1 follows a first thread and generates tracks 1, 3, 5, etc. Target 2 follows a second thread and generates tracks 4, 6, 8, and so on.

On the first rotation of the anode, the scan generated with Target 1 is for tracks 1 and 3. Due to the spacing of the targets, track 2 is skipped and track 4 is generated by Target 2. In the second rotation, Target 1 will cover tracks 5 and 7, and Target 2 will cover tracks 6 and 8. The pattern continues to the end, where the eleventh track is also skipped, similar to track 2, due to the spacing of the targets.

In another embodiment, the first cathode is not turned on until the second rotation of the anode. This will conserve the dose of radiation to the subject and avoid any skipped tracks. The scan will begin with track 4 using Target 2 and Target 1 will be turned on for the second rotation. Therefore, the first rotation will cover track 4 using Target 2, and the second rotation will cover tracks 5 and 7 using Target 1 and tracks 6 and 8 using Target 2. This way none of the tracks are skipped and the area to be imaged 104 is defined beginning with track 3.

The double helical pattern generated during the scan doubles the coverage of the x-ray. Typically, the coverage is limited to 60 mm without compromising the quality of the image. In the present invention, when both cathodes are operational, the coverage is up to 120 mm. Unlike other methods that increase the size of the x-ray coverage area by compromising the quality of the image, the present invention maintains the limit for a quality scanned image, and doubles the area. This is accomplished by using two anodes having back-to-back targets. Each anode has a separate and opposing cathode.

The invention covers all alternatives, modifications, and equivalents, as may be included within the spirit and scope of the appended claims.

What is claimed is:

1. An x-ray tube comprising:
   a body defining a vacuum tube;
   a first anode rotatably mounted within the vacuum tube, said first anode having a back face and a target on a front face,
   a second anode rotatably mounted within the vacuum tube, said second anode having a back face and a target on said front face, said back face of said first anode facing said back face of said second anode wherein said target of said first anode is facing away from said target of said second anode;
   a first cathode mounted in said vacuum tube and facing said target of said first anode; and
   a second cathode mounted in said vacuum tube and facing said target of said second anode.

2. The x-ray tube of claim 1 further comprising a high voltage controller connected to said first and second cathodes for controlling the operation of each of the first and second cathodes.

3. The x-ray tube of claim 1 further comprising said first target face being a fixed distance from said second target face.

4. The x-ray tube of claim 1 further comprising:
   a first heat storage member mounted to said back face of said first anode; and
   a second heat storage member mounted to said back face of said second anode.

5. The x-ray tube of claim 4 further comprising a heat conducting element mounted between and spaced a distance from said first and second heat storage members.

6. The x-ray tube of claim 2 further comprising simultaneous activation of said first and second cathodes.

7. A spiral CT scanner comprising:
   a rotating gantry;
   an x-ray source rotatably mounted to said gantry, said x-ray source having a first anode target facing away from a second anode target, each of said first and second anode targets having a respective cathode adjacent thereto; and
   a detector mounted to said gantry opposite said x-ray source for receiving x-rays from the x-ray source.

8. The spiral CT scanner as claimed in claim 7 wherein said x-ray source further comprises:
   a power supply; and
   a cathode controller connected to said power supply and said first and second cathodes.

9. The spiral CT scanner as claimed in claim 7 wherein said first and second anode targets are spaced a fixed distance from each other.

10. The spiral CT scanner as claimed in claim 7 wherein said detector further comprises;
    a first grid detector mounted to said gantry; and
    a second grid detector mounted to said gantry adjacent to said first grid detector.

11. The spiral CT scanner as claimed in claim 7 further comprising a collimator mounted to said rotating gantry in between said x-ray source and said detector, said collimator for collimating x-ray generated by said x-ray source.

12. The spiral CT scanner as claimed in claim 8 further comprising simultaneous operation of said first and second cathodes.

13. The spiral CT scanner as claimed in claim 8 wherein said x-ray source further comprises:

a first heat storage member mounted to said back face of said first anode; and a second heat storage member mounted to said back face of said second anode.

14. The spiral CT scanner as claimed in claim 13 wherein said x-ray source further comprises a heat conducting element mounted between and spaced a distance from said first and second heat storage members.

15. A method of generating two x-ray beams comprising the steps of:
   rotating a first anode within a vacuum tube, said first anode having a back face and a target on a front face,
   rotating a second anode within the vacuum tube with said first anode, said second anode having a back face and a target on a front face, said back face of said first anode facing said back face of said second anode wherein said target of said first anode is facing away from said target of said second anode;
   generating an electron beam from a first cathode mounted in said vacuum tube and facing said target face of said first anode;
   generating an electron beam from a second cathode mounted in said vacuum tube and facing said target of said second anode;
   focusing said first electron beam on said first anode target to generate a first x-ray beam; and
   focusing said second electron beam on said second anode target to generate a second x-ray beam.

16. The method as claimed in claim 15 further comprising the steps of:
   operating said first and second cathodes simultaneously to generate first and second x-ray beams.

17. The method as claimed in claim 15 further comprising the step of collimating the first and second x-ray beams into a plurality of parallel beams.

18. The method as claimed in claim 15 further comprising the step of maintaining a fixed distance between said first and second anode targets.

19. The method as claimed in claim 15 further comprising the steps of:
   storing heat from said first anode using a first heat storage member mounted to said back face of said first anode; and
   storing heat from said second anode using a second heat storage member mounted to said back face of said second anode.

20. The method of claim 19 further comprising the step of conducting heat away from said first and second heat storage members using a heat conducting element mounted between and spaced a distance from said first and second heat storage members.

21. The method of claim 15 further comprising the step of operating the second cathode before operation of the first cathode to generate a complete scan pattern without skipping tracks.

22. The method as claimed in claim 21 further comprising the steps of:
   operating the second cathode on a first rotation of the anode; and
   operating the first and second cathodes simultaneously after the first rotation of the anode.

* * * * *